(12) United States Patent
Howard et al.

(10) Patent No.: US 6,695,824 B2
(45) Date of Patent: Feb. 24, 2004

(54) WOUND DRESSING SYSTEM

(75) Inventors: Pamela A. Howard, Kersey, CO (US); Eben Howard, Kersey, CO (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/122,374

(22) Filed: Apr. 16, 2002

(65) Prior Publication Data

US 2002/0150720 A1 Oct. 17, 2002

Related U.S. Application Data (60) Provisional application No. 60/283,631, filed on Apr. 16, 2001.

(51) Int. Cl.$^7$ ................................................. A61F 13/00
(52) U.S. Cl. ........................................ 604/305; 604/304
(58) Field of Search ............................... 604/304–308, 604/289; 424/447–449

(56) References Cited

U.S. PATENT DOCUMENTS

| | | | |
|---|---|---|---|
| 4,272,518 A | 6/1981 | Moro et al. | |
| 4,294,241 A | 10/1981 | Miyata | |
| 4,545,371 A | 10/1985 | Grossmann et al. | |
| 4,601,286 A | 7/1986 | Kaufman | |
| 4,684,486 A | 8/1987 | Ricchio | |
| 4,969,880 A | 11/1990 | Zamierowski | |
| 5,029,579 A | 7/1991 | Trammell | |
| 5,145,676 A | 9/1992 | Fahey, III et al. | |
| 5,162,960 A | 11/1992 | Sakata et al. | |
| 5,274,074 A | 12/1993 | Tang et al. | |
| 5,412,068 A | 5/1995 | Tang et al. | |
| 5,636,643 A | 6/1997 | Argenta et al. | |
| 5,645,081 A | 7/1997 | Argenta et al. | |
| 5,695,777 A | 12/1997 | Donovan et al. | |
| 5,725,491 A | 3/1998 | Tipton et al. | |
| 5,817,325 A | 10/1998 | Sawan et al. | |
| 5,848,995 A | 12/1998 | Walder | |
| 5,851,994 A | 12/1998 | Schreiber et al. | |
| 5,990,379 A | 11/1999 | Gregory | |
| 6,040,493 A | 3/2000 | Cooke et al. | |
| 6,045,820 A | 4/2000 | Messier | |
| 6,046,160 A | 4/2000 | Obi-Tabot | |
| 6,083,209 A | 7/2000 | Marasco, Jr. | |
| 6,087,549 A | 7/2000 | Flick | |
| 6,095,992 A | 8/2000 | Augustine | |
| 6,120,789 A | 9/2000 | Dunn | |
| 6,153,214 A | 11/2000 | Horsler | |
| 6,175,053 B1 | 1/2001 | Tsubouchi | |
| 6,179,807 B1 | 1/2001 | Henniges et al. | |
| 6,187,743 B1 | 2/2001 | Obi-Tabot | |
| 6,333,093 B1 | 12/2001 | Burrell et al. | |
| 6,458,109 B1 * | 10/2002 | Henley et al. | 604/304 |

OTHER PUBLICATIONS

Argenta et al., "Vacuum–Assisted Closure: A New Method for Wound Control and Treatment: Clinical Experience," Annals of Plastic Surgery, Jun. 1997, pp. 563–576, vol. 38, No. 6.

Healthpoint Ltd., "Iodosorb Gel & Iodoflex Pad," prinout from http://www.healthpoint.com/mains/wouiod1x.htm dated Mar. 26, 2001.

(List continued on next page.)

Primary Examiner—Weilun Lo
Assistant Examiner—Linh Truong
(74) Attorney, Agent, or Firm—Elizabeth Arwine (57) ABSTRACT

The invention preferably is a wound dressing system having a dressing and an irrigation system in communication with the dressing. The dressing preferably includes a first layer for contacting the wound/injury site of a patient and a second layer that has a backing layer. The backing layer preferably prevents seepage from the wound and/or moisture within the dressing from soiling the surrounding environment.

21 Claims, 6 Drawing Sheets

OTHER PUBLICATIONS

Healthpoint Ltd., "Protocol for Iodosorb Gel & Iodoflex Pad," printout from http://www.healthpoint.com/mains/wouiod2x.htm dated Mar. 26, 2001.

Healthpoint Ltd., "Iodosorb Gel & Iodoflex Pad Prescribing Information," printout from http://www.healthpoint.com/mains/wouiod3x.htm dated Mar. 26, 2001.

Healthpoint Ltd., "How Iodosorb Gel & Iodoflex Pad Works," printout from http://www.healthpoint.com/mains/wouid4x.htm dated Mar. 26, 2001.

Kinetic Concepts, Inc., "Our Products: Vacuum Assisted Closure Pressure Therapy," printout from http://kci1.com/np_therapy.html dated Mar. 21, 2001.

Kinetic Concepts, Inc., "Wound Care Devices: Vacuum Assisted Closure Therapy : The miniV.A.C.," printout from http://kci1.com/mini-vac.html dated Mar. 21, 2001.

Kinetic Concepts, Inc., "Wound Care Devices: Vacuum Assisted Closure Therapy : The V.A.C.," printout from http://kci1.com/the_v.a.c..html dated Mar. 21, 2001.

Kinetic Concepts, Inc., "Wound Management Reference Guide," printout from http://kci1.com/wound_care_reference_guide.html dated Mar. 21, 2001.

Kinetic Concepts, Inc., "What's New with KCI—Kinetic Concepts, Inc. San Antonio TX," printout from http://kci1.com/whats_new.html dated Mar. 21, 2001.

Kinetic Concepts, Inc., "The V.A.C. System" brochure.

LB Hyperbarics, Inc., "TCOM," printout from http://lbhyperbarics.com/tcom.htm dated Apr. 13, 2001.

Radiometer Corp., "Transcutaneous$pO_2/pCO_2$ Monitoring System User's Handbook," pp. 2.1, 2.2, 3.2, 6.1.

Westaim Biomedical, "Westaim Biomedical Overview," printout from http://www.westaimbiomed.com/overview.html, Jan. 18, 2001.

Westaim Biomedical, "Acticoat Product Information," printout from http://www.westaimbiomed.com/acticoat1.html, Jan. 18, 2001.

Westaim Biomedical, "Acticoat Technology," printout from http://www.westaimbiomed.com/acticoat4.html, Jan. 18, 2001.

Westaim Biomedical, "Acticoat Test Results," printout from http://www.westaimbiomed.com/acticoat7.html, Jan. 18, 2001.

Westaim Biomedical, "Acticoat Instructions For Use," printout from http://www.westaimbiomed.com/acticoat2.html, Jan. 18, 2001.

Westaim Biomedical, "Acticoat 7 Product Information," printout from http://www.westaimbiomed.com/acticoat7-overview.html, Jan. 18, 2001.

Westaim Biomedical, "Acticoat 7 Technology," printout from http://www.westaimbiomed.com/acticoat7-tech.html, Jan. 18, 2001.

Yarbrough et al., "Therapeutic and Financial Outcomes Using a Pulsating Low-Air-Loss Surface for Patients Surviving Severe Posterior Burns," Abstract, Ostomy Wound Management, Mar. 2001, vol. 47, Issue 3.

* cited by examiner

WOUND DRESSING SYSTEM

This application claims the benefit of U.S. provisional Application Serial No. 60/283,631, filed Apr. 16, 2001, which hereby is incorporated by reference.

I. FIELD OF THE INVENTION

The present invention is directed to a wound dressing system having an integral wetting system for maintaining the wound in a moist condition.

II. BACKGROUND OF THE INVENTION

It has been found that moist wounds often heal faster. Numerous types of wound dressings have been developed that are designed to maintain a favorable moist environment. For example, an occlusive dressing is designed to keep a wound from being exposed to air, thus reducing evaporation. Many dressings, such as those disclosed in U.S. Pat. Nos. 6,153,214 (Horsier) and 5,695,777 (Donovan et al.) incorporate a water-swellable fiber or intermediate hydrogel layer to promote localized areas containing moisture.

However, these dressings are limited in the kind of fluid used to form the fiber or layer, and, if fluid must be added to the dressing, then the dressings must be constantly tended. Further, pouring water, antibiotic solution, or some other solution on the dressing results in variable wetting and dry spots, both of which may adversely affect wound healing and increase the risk of wound infection and desiccation.

To address uniform wetting, U.S. Pat. No. 6,162,960 (Klein) discloses a compression sponge for dressing a wound having at least one uniform bibulous layer to wick or absorb and retain liquid. The uniform liquid distribution throughout the entire layer provides uniform pressure distribution of any externally applied pressure on the dressing. This type of dressing also requires constant tending, in practice, because it develops dry spots. This type of dressing also is inefficient and ineffective for applying many solutions containing certain therapeutic substances.

A dressing similar to that described in the Klein patent is the Acticoat® Burn Dressing (Westaim Biomedical, Exeter, N.H., U.S.A.). The Acticoat® Burn Dressing includes silver-coated outer layers to protect against infection while the inner core maintains moisture in the dressing. This dressing requires that sterile water be poured on it regularly to provide for continued moisture to be present within the dressing's inner core material. Usually, the Acticoat® Burn Dressing requires water to be wetted down every four to six hours.

The inventors have found that failing to keep the entire wound area moist or wet leads to increased risk of infection and/or dessication of the wound area. To date, no satisfactory dressing has been developed for difficult wounds, such as deep burns or chronic wounds including decubitus ulcers, venous stasis sores, radiation ulcers, pressure sores, ischemic ulcers or diabetic ulcers. Treatment of these wounds remains a very long and expensive process requiring staff to continually and/or frequently monitor the moisture level of a dressing.

Notwithstanding the usefulness of the above-described methods, a need still exists for a dressing that maintains a moist environment with little monitoring by the medical staff required.

III. SUMMARY OF THE INVENTION

A wound dressing system in accordance with the present invention preferably includes a dressing and an irrigation system. The dressing preferably includes a first layer (or wound-contacting layer) and a second or outer layer, which preferably provides a moisture barrier. The irrigation system preferably is interposed between the first layer and the second layer of the dressing. A further embodiment of the invention is a complete system that adds an automated pump to supply the irrigation system.

The absorptive wound dressing system of the invention in its broader aspects preferably includes a laminar structure of three or more layers as follows: a) a porous medical grade polymer material layer that is placed in direct contact with the wound and which is characterized as being wound friendly; b) an intermediate layer including an irrigation system, typically formed of a matrix or assembly of conduits; and c) an outer vapor impermeable layer for maintaining the moisture content within the dressing. Optionally, the first layer may be able to wick or otherwise transfer exudate away from the wound. Also, the outer layer may be of a larger surface area than the other layers so as to include a peripheral skin-contacting adhesive on the underside thereof surrounding the wound area and facilitating contact and covering of the wound.

According to one form of the invention, a wound dressing system including a dressing having a first layer, the first layer including a material suitable for contacting a wound, and a second layer connected to the first layer, the second layer including a backing layer; and an irrigation system in communication with the first layer of the dressing, the irrigation system having at least one conduit.

According to one form of the invention, a wound dressing system including a first layer including material suitable for contacting a wound, a second layer including a backing material attached to the first layer, an irrigation system in communication with the first layer, and a means for providing pressure differential connected to the irrigation system.

According to one form of the invention, a wound dressing including a means for covering a wound, a means for preventing seepage from the dressing, and a means for maintaining wetness within the covering means.

According to one form of the invention, a system including a dressing having a first layer, the first layer including a material suitable for contacting a wound, and a second layer connected to the first layer, the second layer including a backing layer; and an irrigation system in communication with the dressing, the irrigation system having at least one connector, at least one external conduit connected to the connector, the external conduit having a passageway in communication with the connecter, and at least one internal conduit, the internal conduit having a passageway in communication with the passageway of the at least one external conduit and a plurality of holes spaced along the length of the internal conduit, the plurality of holes allowing communication between the passageway of the internal conduit with the first layer of the dressing, the internal conduit forming a pattern within the dressing.

A dressing system in accordance with the present invention may be used for protection of wounds, for infection control, for control of conditions (such as water content, osmolarity, pH, salt concentration, oxygen concentration) in wounds, for thermal regulation, for delivery of bioactive substances (such as nutrients; antibiotics, vasodilatants, vasoconstrictors, steroids and other bioactive substances; growth factors, hormones, enzymes, stimulants and other biomolecules; sulfamylon; silver) into wounds, for removal of harmful substances from wounds, and for protection and support of the human cells proliferating in wounds.

The primary function of the dressing system of the present invention is to occlude the wound, to control its environment, and to promote healing by maintaining the wound area at a certain pre-determined level of moisture content. The dressing system also uniformly distributes moisture or fluid through the wound area, and prevents or reduces the size and number of dry spots covering the wound.

These dressings promote formation of granular tissue in the wound bed, facilitate migration of epidermal cells, and help to control infections. This leads to faster closure of the wound, less pain, and less scarring.

An objective of the invention is to keep the wound and surrounding area (such as bedding and the patient's clothes) clean thus reducing time changing dressings and cleaning the surrounding area.

A further objective of the invention is to reduce the personnel time needed/required to manually keep dressings wet by regularly and frequently checking to see if the dressing is suitably wet and when it is not pouring additional fluid onto the dressing.

A further objective of the invention is to automate the application of fluid to dressings thus decreasing the manpower needed to monitor dressings for wetness.

The accompanying drawings show illustrative embodiments of the invention from which these and other of the objectives, novel features and advantages will be readily apparent. Given the following enabling description of the drawings, the apparatus should become evident to a person of ordinary skill in the art.

IV. BRIEF DESCRIPTION OF THE DRAWINGS

The present invention is described with reference to the accompanying drawings. In the drawings, like reference numbers indicate identical or functionally similar elements.

FIGS. 3(a) and (b) illustrate a top view of different conduit configurations for irrigation systems according to the invention.

FIGS. 5(a) and (b) illustrate side views of different hole patterns for conduits according to the invention.

V. DETAILED DESCRIPTION OF THE DRAWINGS

The present invention as illustrated, for example, in FIGS. 1(a)–(e) is a wound dressing system 50 preferably having a dressing 51 and an irrigation system (or means maintaining wetness within the dressing) 56. The dressing 51 preferably includes a first layer (or means for covering a wound) 52 for contacting the wound area and a second or outer layer (or means for preventing seepage from the dressing) 54, which preferably is fluid impermeable. The irrigation system 56 is preferably disposed between the first layer 52 and the second layer 54 of the dressing 51, or alternatively the irrigation system 56 may be within the first layer 52. An exemplary irrigation system 56 preferably includes a series of interconnected conduits 562 or the like, each conduit 562 having one or more small pores (or holes) 5622 for providing fluid communication with the first layer 52. The irrigation system 56 is configured to provide one or more fluid flow paths for any therapeutically or physiologically desirable or beneficial fluid, including but not limited to air, oxygen, water, an isotonic solution, a hypertonic solution, or the like.

In preferred embodiments of the invention, the irrigation system 56 provides generally uniform distribution of fluid throughout the entire first layer 52. In most preferred embodiments of the invention, the irrigation system 56 provides uniform distribution of fluid across the area of the first layer 52 in contact with or near the wound.

Figure 2:
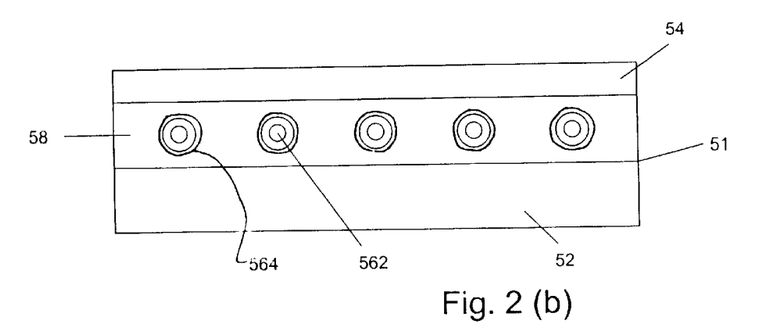
FIG. 2(a) illustrates a cross-section view of an embodiment of the invention illustrating an exemplary irrigation system configuration.
FIG. 2(b) depicts a side view of the embodiment illustrated in FIG. 2(a).
Figure 2A:
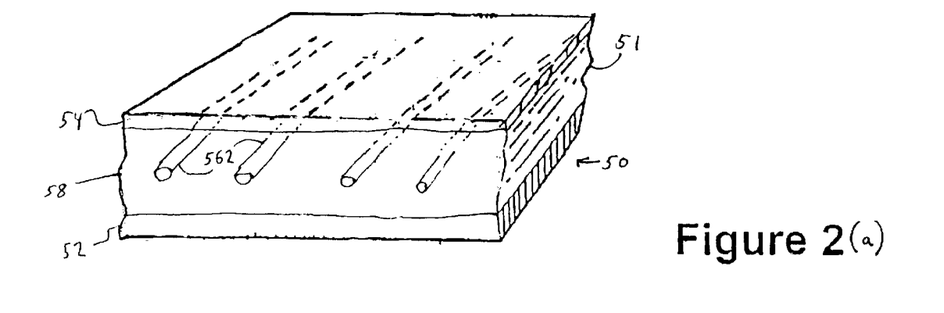

The dressing 51 may also optionally include a moisture retention or reservoir layer 58 positioned between the first layer 52 and the second layer 54 as illustrated in FIGS. 2(a) and (b). The moisture retention layer 58 may also serve to position and/or hold the irrigation system 56 in place within the dressing 51.

The dressing system 50 of the present invention is suitable for use with any wound for which it may be physiologically or therapeutically beneficial to maintain moist, or for which it may be desirable to provide a fluid exchange system.

As used herein, fluid refers to any gaseous or liquid fluid suitable for contact with a wound. Many of these fluids are well known to those skilled in the art. Exemplary fluids include, but are not limited to air, oxygen, water, distilled water, and a saline solution. Fluid also may include a vapor or liquid solution or suspension containing one or more therapeutically beneficial ingredients, including but not limited to one or more antibiotics, antimicrobials, antipathogenic polypeptides, antibacterial and antifungal agents, antiviral agents, steroidal and non-steroidal anti-inflammatory drugs, anti-cancer drugs, anti-clotting agents, anti-tissue damage agents, immune modulators, monoclonal and polyclonal antibodies, hormones, immunosuppressives, thrombolytic agents, vitamins, amino acids, prostaglandins, enzymes, buffers and salts, anions, preservatives, vasodilators; antiarrhythmic agents, cardiotonics, antihypertensives, local anesthetics, hypotensive diuretics, hypnotics and sedatives, central nervous system agents, antitubercular agents, post-cerebral embolism agents, antiulcer agents, preservatives, humectants such as propylene glycol, antimicrobial agents such as silver, pharmaceutical agents, analgesics, non-stick compositions such as silicore emulsions, wound-healing agents, odor-absorbing agents and fragrances, an aqueous alcohol such as an aqueous ethanol; or a sulfamylon solution.

In some embodiments of the invention, the fluid may also include cells or molecules that enhance epidermis growth and/or encourage granulation tissue growth.

In preferred embodiments of the invention, the fluid is water, more preferably saline solution, for example containing from 0.1 to 5.0, often about 0.9, percent by weight sodium chloride, preferably physiological saline. If desired, the aqueous liquor may contain ions which exhibit physiological activity, for example silver or zinc cations. The saline solution may have hypotonic or hypertonic properties depending on its salt content. In the case of burn patient, the fluid preferably is 5% Sulfamylon® solution (Dow B. Hickman, Inc., Sugarland, Tex. U.S.A.).

The fluid may be any temperature. For example, for some therapeutic applications, it may be desirable to alternate between a hot fluid and a cold fluid.

As used herein, adapted for communication, communicating, or similar terms refer to any means, structures, or methods for establishing fluid flow through the system, as are well known by practitioners in the art. For example, a conduit 562 may have a connector 564 adapted to receive or connect to a mated connector on another conduit. As used herein, connector refers to any structure used to form a joint or to join itself to another piece. These connectors or connections establish a fluid flow path through various elements of the apparatus, assembly, or system. Typical connections include but are not limited to mating connections, such as Luer-type, screw-type, friction-type, or connectors that are bonded together.

Figure 1:
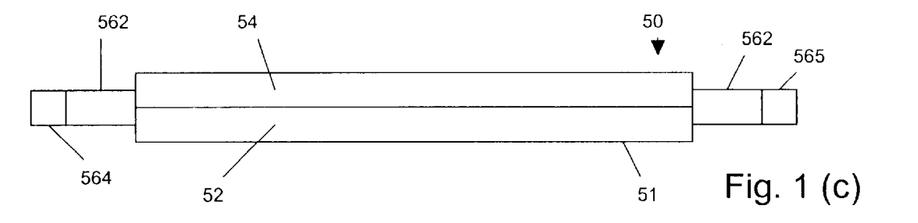
FIG. 1(a) illustrates a schematic cross-section of an embodiment of the invention.
FIG. 1(b) depicts a top view of a preferred embodiment of the invention.
FIG. 1(c) illustrates a side view of the embodiment depicted in FIG. 1(b) with an alternative embodiment of the invention.
FIG. 1(d) illustrates a partial cross-section taken at A—A of the embodiment depicted in FIG. 1(b).
FIG. 1(e) depicts a variety of elements discussed in various embodiments.
Figure 1A:
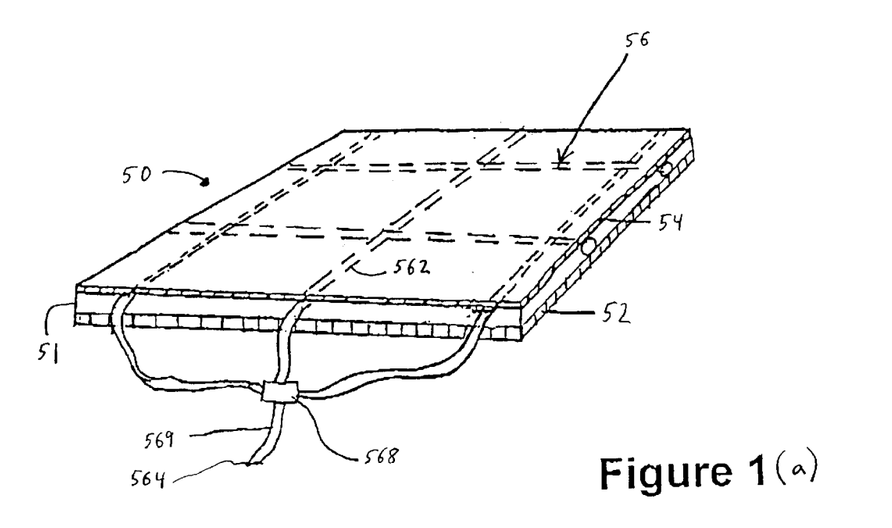
Figure 1B:
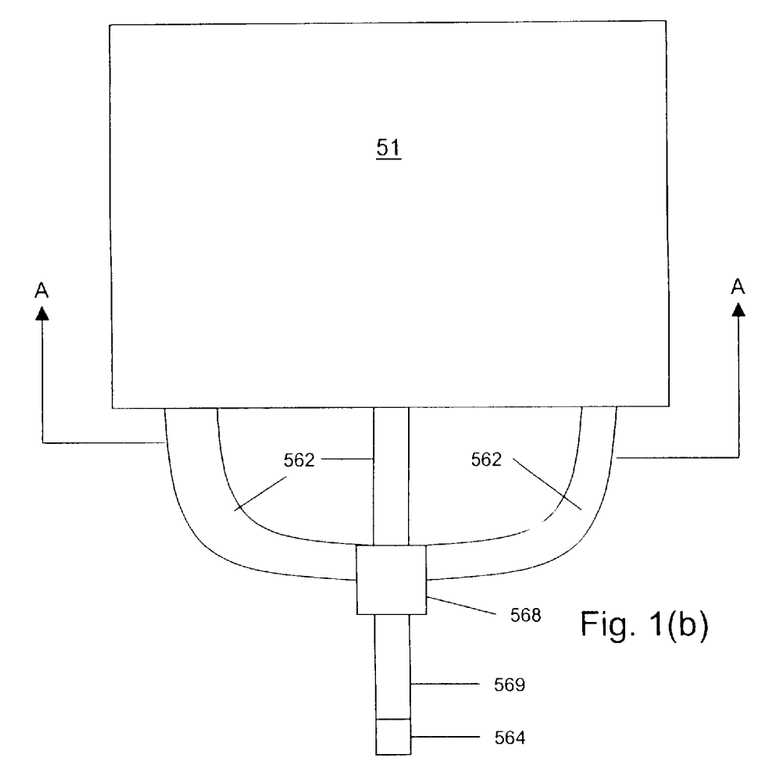
Figure 3:
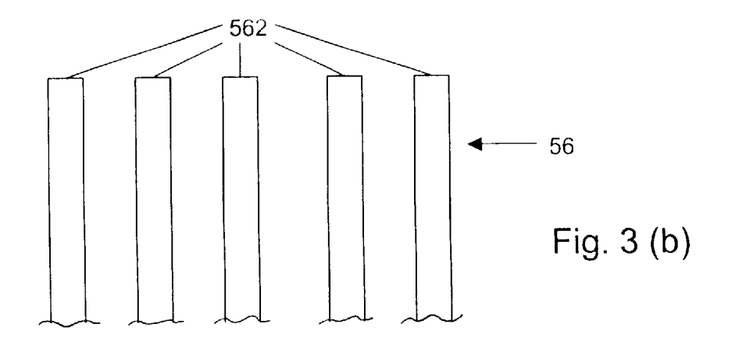

In accordance with the present invention, the irrigation system 56 may be variously configured. In the configuration shown in FIG. 3(a), the conduits 562 communicate with one another within the bandage 50 to form a network of conduits. In preferred embodiments of the invention, the portion of the conduit that is within the dressing includes one or more holes 5622 or the like so that fluid may be transferred between the conduits 562 and the first layer 52. More preferably, the holes 5622 are located from 90 degrees to 270 degrees on conduits 562 where zero degrees is the top 562a and the furtherest portion of each conduit 562 radially from the first layer 52 as illustrated in FIG. 1(d). The irrigation system 56 also preferably includes one or more access ports 564 for delivering fluid to the conduit 562. As described in more detail below, the preferred access port 564 includes a Luer-type fitting (not shown) for connecting to another conduit, to a syringe, or the like. As shown in FIG. 1(b), the irrigation system 56 may also include a manifold (or hub) 568 or the like so that fluid may be administered through a single conduit 569 and distributed throughout the irrigation system 56.

In the configuration illustrated in FIGS. 2(a) and 3(b), the irrigation system 56 includes a series of separate conduits 562. One or both ends of the conduit 562 may include an access port 564. FIG. 2(a) also shows the alternative reservoir layer 58 for retaining moisture within the dressing system 50.

In overall profile, a typical dressing may have a total profile thickness of about 0.70 mm and sufficient surface area to cover a wound. Of course, all of these dimensions can be varied to suit any particular situation or purpose, and can fluctuate greatly depending on the size and number of layers used to form the dressing.

In accordance with the present invention, the dressing system 50 can be applied directly to the wound to protect it and to promote moisture retention and wound healing. The dressing system 50 can be applied dry or wet, i.e., prior to or after adding fluid to the irrigation system 56.

Fluid may be supplied to the irrigation system 56 using any of a number of devices and methods known to those skilled in the art. For example, a syringe or an IV pump may be connected to the system and used to inject fluid into the system. Liquid is supplied to the irrigation system by establishing a pressure differential between the source of the fluid and the other end of the system. A pressure differential may be established using gravity, pressure or a pump, a vacuum, or any other mechanism for moving fluids from one place to another. Any of the ways for establishing the pressure differential may be means for providing pressure differential 60 as depicted in FIG. 1(e). Preferably, the pressure differential is provided by a pump such as an IV pump. Other exemplary sources of fluid are described in more detail below, and each fluid source may be a means for supplying moisture 62 to the maintaining means 56 of the dressing system 50.

Each of the components of a dressing system 50 of the present invention will now be described in more detail.

The first layer 52 may be variously configured. In preferred embodiments of the invention, the first layer 52 includes a fine mesh absorbent facing with multi-layered cellulose. It has been found that such a configuration promotes maximum absorbency. This material preferably has wicking characteristics, which have been found to be especially desirable in wound dressings to be used on wounds which require draining.

The first layer 52 may for example, be a porous fabric or mesh such as the screen fabrics or filter fabrics of polyethylene, polypropylene, nylon or polyester. Any of a variety of polymeric materials may be used. The choice of suitable material and pore size or the like for transfer in the first layer 52 will be dictated by the needs of the patient. In addition, the material preferably is flexible, soft, conformable, non-irritating, non-sensitizing, and non-cytotoxic.

The first layer 52 may include an antibacterial or other therapeutic agent, and may be configured into a pattern, such as a waffle contour, for greater comfort, and/or with a thicknesses exhibiting desired characteristics of porosity, density, and the like in accord with optimum wound treatment. In particular, a smooth, unwrinkled, compressible layer can significantly contribute toward reduction of bruising. The first layer 52 may include a silver coating (such as that found in the Acticoat® Burn Dressing) that allows continuous application of silver to a wound over a period of time.

Similarly, the wound contacting surface or first layer 52 can be further modified to include therapeutic agents such as biologically active substances to promote healing which are bound to the structure of the wound dressing.

It is intended that the present invention should not be limited by the type, form, or construction of a particular first layer 52.

In preferred embodiments of the invention, the second layer 54 is a moisture barrier. The primary functions of the second layer 54 are to protect the underlying structures from mechanical damage, from contamination and from a gross loss of liquids.

It may be desirable that the second layer 54 is transparent or does not obstructed a view of the wound. Examples of suitable materials for the second layer 54 are polyolefines, soft acrylic resins, polyurethanes, plasticized PVC, silicone and other synthetic elastomers, and substantially impermeable plastic foil.

Figure 4:
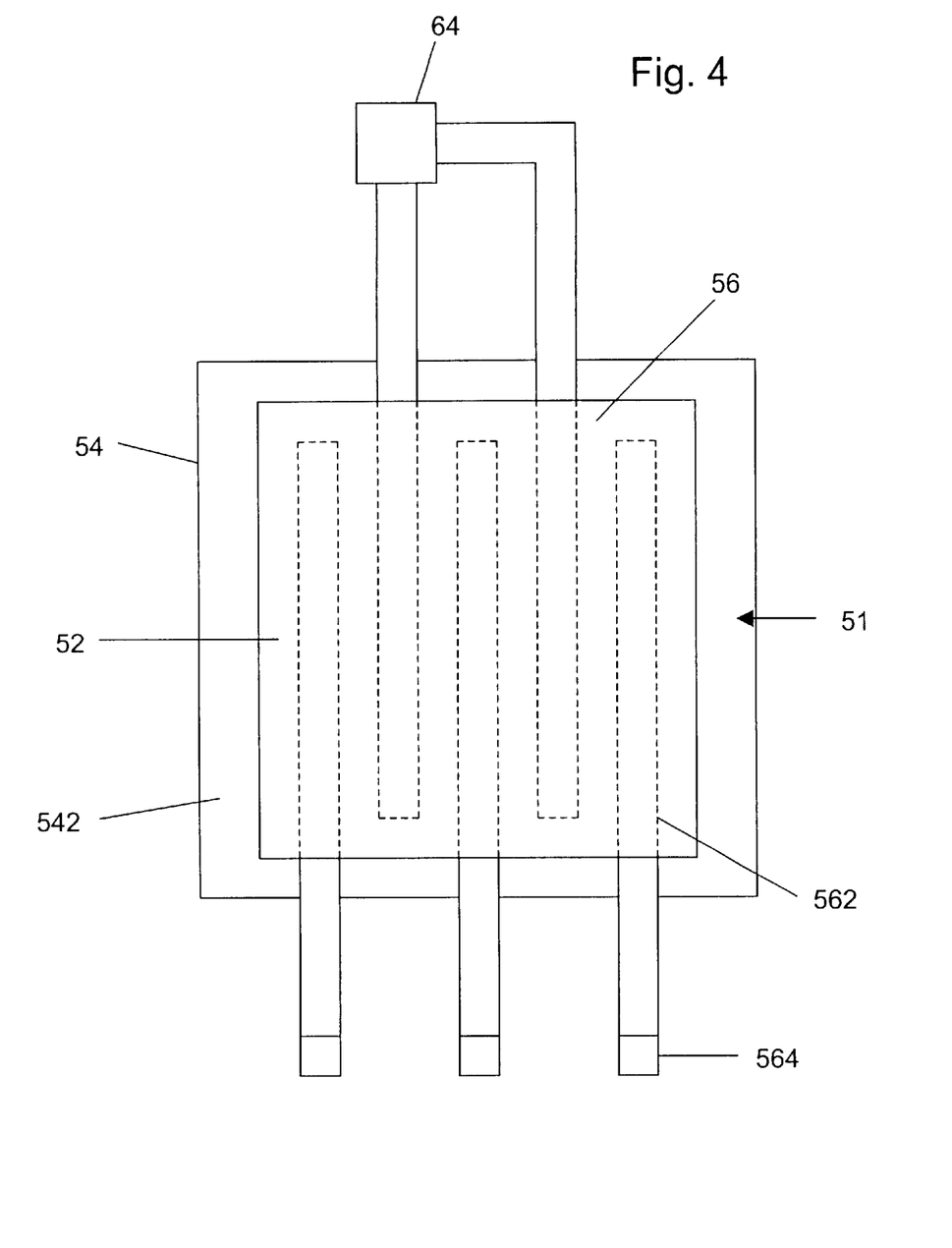
FIG. 4 depicts a top view of different alternative embodiments according to the invention.

The second layer 54 in an alternative embodiment has a larger footprint area than the other layer(s) in the dressing system 50. As illustrated in FIG. 4, the extra area can be covered with a suitable skin adhesive 542 for fixing the dressing and sealing the wound. A quantity of adhesive 542 may be included on the exposed peripheral underside of second layer 54. Such adhesives as Monsanto 612 or Flexcon adhesive H-566 are suitable for this purpose. The adhesive 542 should be hypoallergenic and designed for prolonged use on human skin.

The irrigation system 56 preferably includes flexible tubing for the conduit(s) 562. As used herein, the tubing may be any conduit or means which provides fluid communication from a source of fluid to one or more areas in the dressing system 50. The tubing or conduit 562 preferably is a flexible plastic, more preferably plasticized PVC, or other conventional polymer. The construction of such conduits are well known to those skilled in the art.

In accordance with the present invention, the conduit 562 may alternatively be formed of a hydrogel or some other high water content moiety. For example, the conduit 562 may be formed of a hydrophilic polyurethane hydrogel of the composition described in the U.S. Pat. No. 5,120,816 (Gould et al.).

There may be a number of tubes 562 providing fluid communication to any individual area within the dressing system 50, and the tubes 562 may be oriented in a number of ways. For example, FIGS. 1(*a*) and 3(*a*) illustrate a unitary matrix of conduits 562, while FIGS. 2(*a*) and 3(*b*) illustrate a series of individual conduits 562. In another exemplary embodiment (not shown), the configurations in FIGS. 3(*a*) and (*b*) may be combined where passageways in perpendicular conduits do not communicate with each other. Additionally, the tubes and conduit assemblies may be oriented to define different flow paths such as having fluid provided from more than one side (or portion if the dressing is non-polygonal or has non-polygonal areas). Furthermore although one, three, four and five conduits are illustrated in the Figures, the number and arrangement of the conduits preferably is selected based upon the size and purpose for the dressing.

Figure 5:
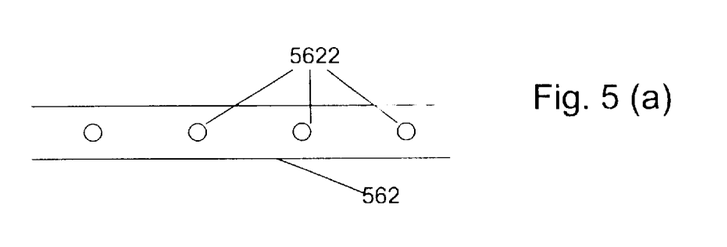

The portions of the conduit(s) 562 inside the dressing material preferably include one or more holes 5622 so that fluid in the conduit 562 can wet the first layer 54. It is intended that the invention should not be limited by the size or number of holes 5622 in the conduit 562. One skilled in the art will readily recognize that the number and size of the holes 5622 may be dependent on the type of wound, on the size of the dressing, or other factors. It has been found that placing a hole 5622 every centimeter or so provides suitable wetting and fluid dispersion across the first layer 52. The approximate centimeter distance between holes 5622 preferably also is the absolute distance between holes irrespective of a particular conduit 562. FIGS. 5(*a*) and (*b*) illustrate two exemplary hole patterns for positioning holes 5622 on a particular conduit 562.

The irrigation system 56 preferably includes an access port 564 for delivering and/or removing fluid from the conduit 562 within the dressing system 50. An exemplary embodiment is shown in FIGS. 1(*a*) and (*b*). The irrigation system 56 may also include multiple access ports 564 as illustrated in FIGS. 2(*a*) and (*b*).

The ends of each conduit 562 may be capped or closed, or open or openable. In some embodiments of the invention, the conduit end opposite the access port 564 is sealed and positioned within the dressing 51. In other embodiments of the invention, the conduit end opposite the access port 564 passes through the dressing 51 as illustrated in FIG. 1(*c*), which illustrates a capped end 565. In this embodiment of the invention, the end 565 preferably is capped and openable, and alternatively may include a fitting such as a Luer-lock for attachment to, for example, other conduits, a container, or a pump. For example, the end 565 of the conduit may be in fluid communication with a vacuum suitable for drawing fluid into the dressing, or for drawing fluid or exudate in the dressing 51 out of the dressing 51. In an alternative embodiment, a filter may be placed on the outlet conduit to avoid any organisms getting into the system.

A cap, closure, seal, valve, clamp, transfer leg closure, or the like is typically located in or on the conduit. It is intended that the present invention is not limited by the type of material used to construct the conduit. The ends of the conduit may be attached to an infusion set for administering or changing the solution in the conduit as required.

Figure 6:
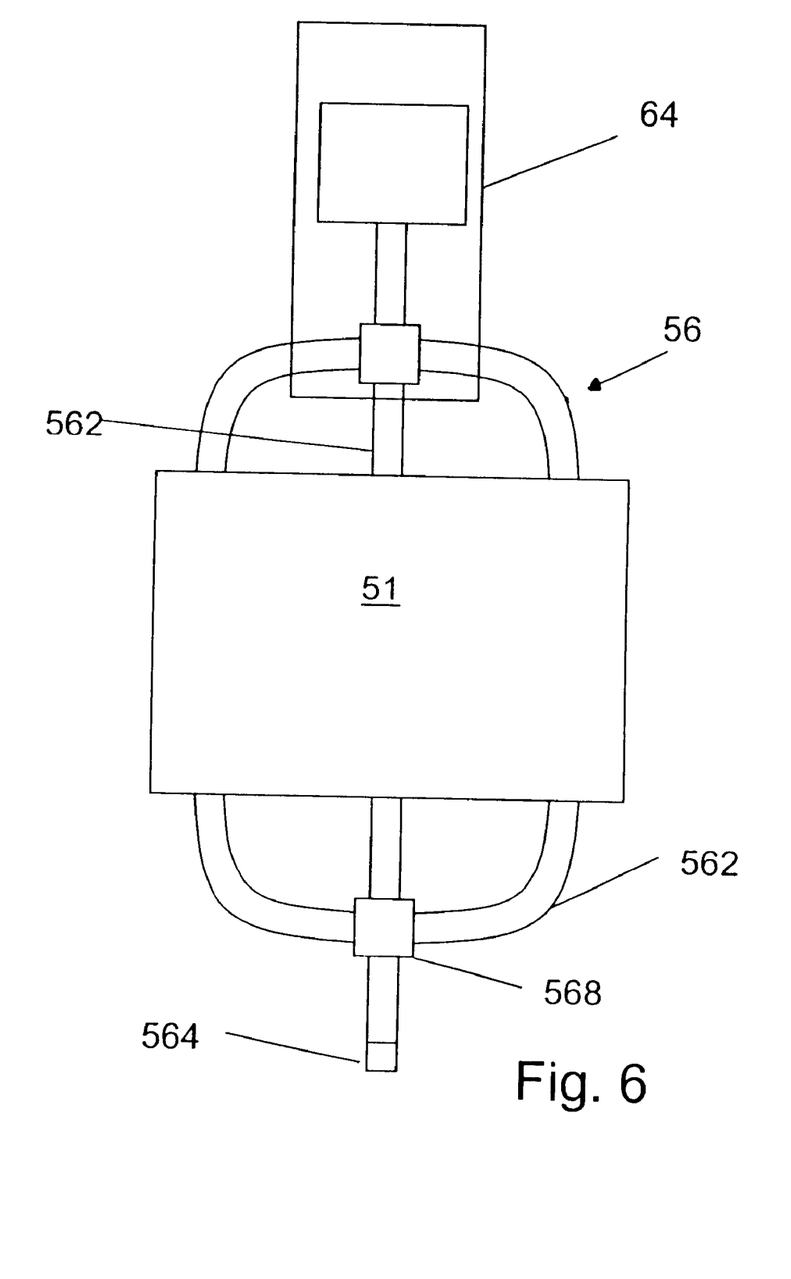
FIG. 6 depicts a top view of an alternative embodiment according to the invention.

The dressing system 50 in an alternative embodiment is connected to a vacuum system 64 to remove exudates away from the wound. The vacuum system may be connected to the irrigation system 56 (illustrated in FIG. 6) and/or a separate irrigation system 56' (illustrated in phantom in FIG. 4) for removal purposes. Preferably in this embodiment, the separate conduit system 56' would mirror the configuration/layout/design of the irrigation system 56.

In another alternative embodiment, the first layer includes a slow release substance and/or fluid like, for example, an antibiotic and/or silver. Preferably, the added material will be slowed released from the dressing. Additionally, the added material may be activated by the moisture present within the dressing system 50.

Another alternative embodiment would have the first layer be removable from the rest of the dressing to allow replacement of the first layer to reduce the cost of use. Preferably in this alternative embodiment, the first layer is attached to the rest of the dressing such that it may be easily removable while preventing leakage of fluid from the dressing sides. One possibility is to have the surface area of the first layer capable of folding around the edges of the dressing and attaching to the backside of the dressing with Velcro.

Another alternative embodiment as depicted in FIG. 1(*e*) adds a feedback system 66 such as an electric resistance feedback system built into the dressing 51. The feedback system 66 preferably monitors the level of moisture in the wound bed. The feedback system 66 may include Drager (or Draeger) tubes built into the dressing 51 to detect certain organisms that may be in the wound bed, to allow the feedback system to instruct a pump 60 to pump antibiotics through the irrigation system 56 into the dressing 51 and/or notify medical personnel of the presence of certain organisms preferably including identification of the type of organism.

In use, the dressing system 50 preferably is placed over a wound, and can be held in place by an overlaying elastic garment (not shown), by adhesive tape strips (not shown) bridging from the dressing system 50 to surrounding skin, by adhesive double-faced tape pieces, or by any other dressing method as recognized in the art. Alternatively, the dressing system 50 may be held in place by adhesive 542 when present. Thus, if the dressing system 50 is used to treat the site of a burn, minimal or no adhesive material is used, and the dressing system 50 preferably is held in place in any manner that a physician determines as most comfortable for a patient.

Once the dressing system 50 is in place, a source of fluid such as a bag or syringe containing saline solution may be connected to one or more conduits 562 through at least one port 564. The fluid may then be pumped or drawn into the conduits 562, where the fluid passes through the holes 5622 and wets the first layer 52.

The dressing 51 also may be of sufficient size to cover the entire bed. Alternatively, the dressing 51 may be in the form of a sock and/or mitten to cover an extremity. A further alternative shape for dressing 51 is to be any shape or size to cover any particular body part.

The dressing system 50 may also be packaged by sealing into a water-impermeable plastic pouch and sterilized by gamma irradiation or other suitable sterilization technique.

Although the present invention has been described in terms of particular preferred and alternative embodiments, it is not limited to those embodiments. Alternative embodiments, examples, and modifications which would still be encompassed by the invention may be made by those skilled in the art, particularly in light of the foregoing teachings.

Those skilled in the art will appreciate that various adaptations and modifications of the preferred and alternative embodiments described above can be configured without departing from the scope and spirit of the invention. Therefore, it is to be understood that, within the scope of the appended claims, the invention may be practiced other than as specifically described herein.

We claim:

1. A wound dressing system comprising:
   a dressing having
      a first layer, said first layer including a material suitable for contacting a wound, and
      a second layer connected to said first layer, said second layer including a backing layer, and
   an irrigation system in communication with said first layer of said dressing, said irrigation system having at least one conduit; and
   wherein said irrigation system is between said first layer and said second layer, and said irrigation system includes a matrix of interconnected conduits.

2. The wound dressing system of claim 1, wherein said irrigation system further includes at least one connector in communication with said at least one conduit.

3. The wound dressing system of claim 2, wherein a portion of said conduit in said dressing further includes at least one hole.

4. The wound dressing system of claim 1, wherein said first layer includes a silver coating.

5. The wound dressing system of claim 1, further comprising a means for providing pressure differential connected to said irrigation system.

6. The wound dressing system according to claim 5, wherein said pressure differential means includes a pump.

7. The wound dressing system according to claim 6, wherein said irrigation system includes a portion within said first layer.

8. The wound dressing system according to claim 5, wherein said pressure differential means includes a vacuum.

9. The wound dressing system according to claim 8, comprising a second conduit system connected to said vacuum, and
   wherein said irrigation system includes a first conduit.

10. The wound dressing system according to claim 5, wherein said first layer includes silver.

11. A wound dressing system comprising:
    a dressing having
       a first layer, said first layer including a material suitable for contacting a wound, and
       a second layer connected to said first layer, said second layer including a backing layer, and
    an irrigation system in communication with said first layer of said dressing, said irrigation system having at least one conduit and at least one connector in communication with said at least one conduit; and
    wherein said irrigation system is between said first layer and said second layer, and
    said irrigation system includes a series of individual conduits.

12. The wound dressing system according to claim 11, wherein said first layer includes silver.

13. A wound dressing system comprising:
    a dressing having
       a first layer, said first layer including a material suitable for contacting a wound, and
       a second layer connected to said first layer, said second layer including a backing layer, and
    an irrigation system in communication with said first layer of said dressing, said irrigation system having at least one conduit and at least one connector in communication with said at least one conduit: and
    wherein said irrigation system is between said first layer and said second layer, and
    a portion of said conduit in said dressing includes a plurality of drain holes.

14. The wound dressing system according to claim 13, wherein said first layer includes silver.

15. A wound dressing system comprising:
    a dressing having
       a first layer, said first layer including a material suitable for contacting a wound,
       a second layer connected to said first layer, said second layer including a backing layer, and
       a third layer having a reservoir, said third layer is between said first layer and said second layer; and
    an irrigation system in communication with said first layer of said dressing, said irrigation system having at least one conduit.

16. The wound dressing system of claim 15, further comprising a means for providing pressure differential connected to said irrigation system.

17. The wound dressing system according to claim 16 herein said pressure differential means includes a pump.

18. The wound dressing system according to claim 16, wherein said pressure differential means includes a vacuum.

19. The wound dressing system according to claim 18, further comprising a second conduit system connected to said vacuum, and wherein said irrigation system includes a first conduit.

20. A system comprising:
    a dressing having
       a first layer, said first layer including a material suitable for contacting a wound, and
       a second layer connected to said first layer, said second layer including a backing layer, and
    an irrigation system in communication with said dressing, said irrigation system having
       at least one connector,
       at least one external conduit connected to said connector, said external conduit having a passageway in communication with said connecter, and
       at least one internal conduit, said internal conduit having a passageway in communication with the passageway of said at least one external conduit and a plurality of holes spaced along the length of said internal conduit, the plurality of holes allowing communication between the passageway of said internal conduit with said first layer of said dressing, said internal conduit forming a pattern within said dressing.

21. The wound dressing system according to claim 20, wherein said first layer includes silver.

* * * * *